(12) United States Patent
Sanders et al.

(10) Patent No.: US 10,138,519 B2
(45) Date of Patent: Nov. 27, 2018

(54) UNIVERSAL SANGER SEQUENCING FROM NEXT-GEN SEQUENCING AMPLICONS

(71) Applicant: Quest Diagnostics Investments Incorporated, Wilmington, DE (US)

(72) Inventors: Heather Sanders, San Juan Capistrano, CA (US); Hai-Rong Li, San Juan Capistrano, CA (US); Feras Hantash, San Juan Capistrano, CA (US); Frederic Waldman, San Juan Capistrano, CA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 366 days.

(21) Appl. No.: 14/655,103

(22) PCT Filed: Dec. 27, 2013

(86) PCT No.: PCT/US2013/078039
§ 371 (c)(1),
(2) Date: Jun. 24, 2015

(87) PCT Pub. No.: WO2014/106076
PCT Pub. Date: Jul. 3, 2014

(65) Prior Publication Data
US 2015/0344948 A1    Dec. 3, 2015

Related U.S. Application Data

(60) Provisional application No. 61/747,062, filed on Dec. 28, 2012.

(51) Int. Cl.
C12Q 1/68 (2018.01)
C12Q 1/6876 (2018.01)
C12Q 1/6869 (2018.01)

(52) U.S. Cl.
CPC ......... *C12Q 1/6876* (2013.01); *C12Q 1/6869* (2013.01); *C12Q 2600/16* (2013.01)

(58) Field of Classification Search
None
See application file for complete search history.

(56) References Cited

U.S. PATENT DOCUMENTS

| | | | |
|---|---|---|---|
| 2002/0006666 | A1 | 1/2002 | Matsumoto |
| 2004/0023207 | A1* | 2/2004 | Polansky ............... A61K 31/00 435/5 |
| 2010/0273219 | A1 | 10/2010 | May et al. |

OTHER PUBLICATIONS

GenBank Accession No. NC_018915 (abridged) [online] Jun. 6, 2016 [retrieved on Jun. 21, 2017] retrieved from https://www.ncbi.nlm.nih.gov.*
Schlipf et al., "Amplicon-based high-throughput pooled sequencing identifies mutations in CYP7B1 and SPG7 in sporadic spastic paraplegia patients," Clin. Genetics, vol. 80, No. 2, pp. 148-160, Aug. 2011.

(Continued)

*Primary Examiner* — Saumel C Woolwine
(74) *Attorney, Agent, or Firm* — Foley & Lardner LLP

(57) ABSTRACT

Described herein are methods, compositions and kits directed to amplification of nucleic acids suitable for both next generation sequencing (NGS) and a second round of sequencing as validation, such as Sanger sequencing.

18 Claims, 5 Drawing Sheets

Specification includes a Sequence Listing.

(56) References Cited

OTHER PUBLICATIONS

Dana-Farber Cancer Institute, "Oligo Calculator," Molecular Biology Core Facility [online], http://mbcf.dfci.harvard.edu/docs/oligocalc.html, retrieved Apr. 16, 2014.
Baetens et al, "Applying massive parallel sequencing to molecular diagnosis of Marfan and Loeys-Dietz syndromes," Hum Mutat, vol. 32, No. 9, pp. 1053-1062, Sep. 2011.
Daigle et al., "High-Throughput Sequencing of PCR Products Tagged with Universal Primers Using 454 Life Sciences Systems," Current Protocols in Molecular Biology, Unit 7.5, pp. 1-14, Oct. 2011.
International Search Report dated Jul. 14, 2014 in application No. PCT/US2013/078039.

* cited by examiner

SEQUENCE LISTING

<160> NUMBER OF SEQ ID NOS: 87

<210> SEQ ID NO 1
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
gtaaaacgac ggccagt                                                  17

<210> SEQ ID NO 2
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
aacagctatg accatg                                                   16

<210> SEQ ID NO 3
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
atttaggtga cactatag                                                 18

<210> SEQ ID NO 4
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
cagtcaagta acaaccgcga                                               20

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtaaaacgac ggccagtatt taggtgacac tatag                              35

<210> SEQ ID NO 6
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
aacagctatg accatgcagt caagtaacaa ccgcga                             36

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
acactgacga catggttcta ca                                          22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tacggtagca gagacttggt ct                                          22

<210> SEQ ID NO 9
<211> LENGTH: 57
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
gtaaaacgac ggccagtatt taggtgacac tatagacact gacgacatgg ttctaca     57

<210> SEQ ID NO 10
<211> LENGTH: 58
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
aacagctatg accatgcagt caagtaacaa ccgcgatacg gtagcagaga cttggtct    58

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
caggaaacag ctatgac                                                17

<210> SEQ ID NO 12
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gttttcccag tcacgac                                                17

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cggataacaa tttcacacag                                              20

<210> SEQ ID NO 14
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gtaaaacgac ggccagtg                                                18

<210> SEQ ID NO 15
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctgtaaatca acaacgcaca g                                            21

<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
gcaaatggca ttctgacatc c                                            21

<210> SEQ ID NO 17
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gactggttcc aattgacaag c                                            21

<210> SEQ ID NO 18
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tactattgcc agcattgctg c                                            21

```
<210> SEQ ID NO 19
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
ggatctcgac gctctccct                                                    19

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtttgtacaa aaaagcaggc                                                   20

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
ccactttgta caagaaagct gggt                                               24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
cgcgttaacg ctagcatgga tctc                                               24

<210> SEQ ID NO 23
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
catcagagat tttgagacac                                                   20

<210> SEQ ID NO 24
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
tcatcggaag agagtag                                                       17

<210> SEQ ID NO 25
```

```
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 25
cgttttaaaa cctaagagtc a                                              21

<210> SEQ ID NO 26
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
gggtcaagga aggcacg                                                   17

<210> SEQ ID NO 27
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
tagaaggcac agtcgagg                                                  18

<210> SEQ ID NO 28
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgcaaatggg cggtaggcgt g                                              21

<210> SEQ ID NO 29
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gattatgcgg ccgtgtacaa                                                20

<210> SEQ ID NO 30
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
tcaagcctca gacagtggtt c                                              21

<210> SEQ ID NO 31
<211> LENGTH: 22
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 31
catggtcctg ctggagttcg tg                                               22

<210> SEQ ID NO 32
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
gttcaggggg aggtgtg                                                     17

<210> SEQ ID NO 33
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
cgtcgccgtc cagctcgacc ag                                               22

<210> SEQ ID NO 34
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
attttcggtt tgtattactt c                                                21

<210> SEQ ID NO 35
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
taccactaca atggatg                                                     17

<210> SEQ ID NO 36
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
tgtatcttat ggtactgtaa ctg                                              23

<210> SEQ ID NO 37
<211> LENGTH: 23
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 37
ctttatgttt ttggcgtctt cca                                              23

<210> SEQ ID NO 38
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38
tccgtaggtg aacctgcgg                                                   19

<210> SEQ ID NO 39
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39
tcctccgctt attgatatgc                                                  20

<210> SEQ ID NO 40
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40
tcgtaacaag gtttccgtag gtg                                              23

<210> SEQ ID NO 41
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41
tcgaggtcga cggtatc                                                     17

<210> SEQ ID NO 42
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42
ggtcgtcaga ctgtcgatga agcc                                             24

<210> SEQ ID NO 43
<211> LENGTH: 20
<212> TYPE: DNA
<213> ORGANISM: Artificial Sequence
```

<220> FEATURE:
<223> OTHER INFORMATION: Description of Artificial Sequence: Synthetic
      primer

<400> SEQUENCE: 43
cgcaacgatc tggtaaacac                                            20

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44
gacaatacaa actaagattt agct                                       24

<210> SEQ ID NO 45
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 45
atgccatagc atttttatcc                                            20

<210> SEQ ID NO 46
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 46
gatttaatct gtatcagg                                              18

<210> SEQ ID NO 47
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 47
agagctcgtt tagtgaaccg                                            20

<210> SEQ ID NO 48
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 48
gtggtttgtc caaactcatc                                            20

<210> SEQ ID NO 49
<211> LENGTH: 24
<212> TYPE: DNA
<213> ORGANISM: Artificial Sequence
<220> FEATURE:

```
<223> OTHER INFORMATION: Description of Artificial Sequence: Synthetic
      primer

<400> SEQUENCE: 49
gtaacatcag agattttgag acac                                            24

<210> SEQ ID NO 50
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 50
gtttctacaa actcttcctg                                                 20

<210> SEQ ID NO 51
<211> LENGTH: 16
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atgcgtccgg cgtaga                                                     16

<210> SEQ ID NO 52
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
gttaaattgc taacgcagtc a                                               21

<210> SEQ ID NO 53
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tcacgacgtt gtaaaacgac                                                 20

<210> SEQ ID NO 54
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
cataccgtcc caccatcg                                                   18

<210> SEQ ID NO 55
<211> LENGTH: 20
<212> TYPE: DNA
<213> ORGANISM: Artificial Sequence
<220> FEATURE:
<223> OTHER INFORMATION: Description of Artificial Sequence: Synthetic
``` primer

<400> SEQUENCE: 55
atcctctagt acttctcgac                                                  20

<210> SEQ ID NO 56
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
ccgggagctg catgtgtcag agg                                              23

<210> SEQ ID NO 57
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
tggacccaat gtgcctg                                                     17

<210> SEQ ID NO 58
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 58
gggctggcaa gccacgtttg gtg                                              23

<210> SEQ ID NO 59
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
ctcgtatgtt gtgtggaatt gtgagc                                           26

<210> SEQ ID NO 60
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
catatagaca aacgcacac                                                   19

<210> SEQ ID NO 61
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
gatgcctcct acccttatga tgtgcc        26

<210> SEQ ID NO 62
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62 ttttttttttt tttttttttt tttv        24

<210> SEQ ID NO 63
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
cccgaaaagt gccacctg        18

<210> SEQ ID NO 64
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 64
gttctgaggt cattactg        18

<210> SEQ ID NO 65
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gctcgataca ataaacgcc        19

<210> SEQ ID NO 66
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
ggtctatata agcagagctg        20

<210> SEQ ID NO 67
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 67
gtggtatggc tgattatgat cag                                              23

<210> SEQ ID NO 68
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gacatcataa cggttctg                                                    18

<210> SEQ ID NO 69
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
ctgagttcgg catgggg                                                     17

<210> SEQ ID NO 70
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gaggtatata ttaatgtatc g                                                21

<210> SEQ ID NO 71
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
gatttaatct gtatcagg                                                    18

<210> SEQ ID NO 72
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
ctagcaaaat aggctgtccc                                                  20

<210> SEQ ID NO 73
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
```
gacgatagtc atgccccgcg                                          20

<210> SEQ ID NO 74
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
cgaacgccag cacatggaca                                          20

<210> SEQ ID NO 75
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgctctagaa ctagtggatc                                          20

<210> SEQ ID NO 76
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
atttaggtga cactatag                                            18

<210> SEQ ID NO 77
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77 attaccctc actaaaggga                                           20

<210> SEQ ID NO 78
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 78
tagttattgc tcagcggtgg                                          20

<210> SEQ ID NO 79
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79 aaccccctcaa gacccgttta                                      20

<210> SEQ ID NO 80
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
taatacgact cactataggg                                       20

<210> SEQ ID NO 81
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ctagttattg ctcagcgg                                         18

<210> SEQ ID NO 82
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
ttcctcgacg ctaacctg                                         18

<210> SEQ ID NO 83
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
gttttcccag tcacgacgt                                        19

<210> SEQ ID NO 84
<211> LENGTH: 47
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
ctctctcggt cagtctgtgy ctaggycttg yagatctgtg tgttccg          47

<210> SEQ ID NO 85
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
ctctctcggt cagtctgcgy gttyggtctt gyagatctgt gtgttccg         48

<210> SEQ ID NO 86
<211> LENGTH: 203
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 86
tagactgtcg tacatggttc acatttccac agctacacca tatctgaatg gagaaacatc    60
tacaaaatcc ctttgggtta taaatactcc actcagaata aaattctttg tggaacctac   120
gtcaatgtaa atattcgaga cattgataag gtaaactcaa atgctgatgg agaccaagtg   180
tctggtaccg tatcgcggtt gtt                                           203

<210> SEQ ID NO 87
<211> LENGTH: 232
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 87
acgcgatcgg tagcagagac ttggtctgca tcagcatttg actttacctt atcaatgtct    60
cgaatattta cattcacgta ggttccacaa agaatttta ttctgagtgc actatttata   120
acccaaaggg attttgtaga tgtttctcat tcatatatgg tgtacctgtg gaaattgtac   180
aaccatgtcg tcagtgtcta tactgtcacc taaatactgg ccgtcgttta ac          232

UNIVERSAL SANGER SEQUENCING FROM NEXT-GEN SEQUENCING AMPLICONS

TECHNICAL FIELD

The present technology relates to primers and related methods for providing separate validation of the sequence of amplicons designed also for sequence determination by next-generation sequencing (NGS) methods.

BACKGROUND

The following description is provided to assist the understanding of the reader. None of the information provided or references cited is admitted to be prior art to the present invention.

DNA Sequencing

The chain-termination method (also called Sanger sequencing, after the developer) is the dominant method of sequencing. The classical chain-termination method requires a single-stranded DNA template, a DNA primer, a DNA polymerase, normal deoxynucleotidetriphosphates (dNTPs), and modified nucleotides (dideoxyNTPs) that terminate DNA strand elongation. These chain-terminating nucleotides lack a 3'-OH group required for the formation of a phosphodiester bond between two nucleotides, causing DNA polymerase to cease extension of DNA when a ddNTP is incorporated. The ddNTPs may be radioactively or fluorescently labeled for detection in automated sequencing machines. There are a number of "universal sequencing primers" which are incorporated into plasmids for convenient generation of sequencing constructs. Such primers are generally available for free or at relative low prices.

Modifications of the basic Sanger method, and increased automation, have been the foundation for most genomic sequencing.

Next Generation Sequencing

DNA sequencing technologies have advanced exponentially. Most recently, high-throughput sequencing (or next-generation sequencing) technologies parallelize the sequencing process, producing thousands or millions of sequences at once. In ultra-high-throughput sequencing as many as 500,000 sequencing-by-synthesis operations may be run in parallel. Next-generation sequencing lowers the costs and greatly increases the speed over the industry standard dye-terminator methods.

Massively Parallel Signature Sequencing (MPSS) was one of the earlier next-generation sequencing technologies. MPSS uses a complex approach of adapter ligation followed by adapter decoding, reading the sequence in increments of four nucleotides. This method made it susceptible to sequence-specific bias or loss of specific sequences.

Polony sequencing combined an in vitro paired-tag library with emulsion PCR, an automated microscope, and ligation-based sequencing chemistry to sequence an *E. coli* genome. The technology was incorporated into the Applied Biosystems SOLiD platform.

454 pyrosequencing amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence read-outs.

In Solexa sequencing DNA molecules and primers are first attached on a slide and amplified with polymerase so that local clonal colonies, initially coined "DNA colonies", are formed. To determine the sequence, four types of reversible terminator bases (RT-bases) are added and non-incorporated nucleotides are washed away. Unlike pyrosequencing, the DNA chains are extended one nucleotide at a time and image acquisition can be performed at a delayed moment, allowing for large arrays of DNA colonies to be captured by sequential images taken from a single camera.

SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Solexa sequencing.

Validation

While next-generation sequence methods are faster and cheaper than traditional methods, there remain questions as to their accuracy. Accuracy is particularly important in human clinical diagnostics, where significant medical decisions may hinge on a single nucleotide polymorphism.

In view of the higher fidelity requirements for diagnostic applications, recent clinical guidelines have mandated that all mutations identified by next-generation sequencing must be validated on an alternative platform before reporting the results, such as the Sanger method. See, e.g. www.oseh-ra.org/blog/big-news-next-generation-sequencing-guide-lines-issued-college-american-pathologists, Aug. 1, 2012; see also, American College of Medical Genetics *ACMG Standards and Guidelines for Clinical Laboratories*.

SUMMARY OF THE INVENTION

Described herein are methods, compositions, and kits for the amplification and sequencing of nucleic acids, particularly in conjunction with next-generation sequencing.

In one embodiment, the present disclosure provides a composition comprising a first oligonucleotide that comprises, in 5' to 3' order, (a) a first region suitable for use as a sequencing primer (e.g., a Sanger sequencing primer); (b) a spacer that is between about 5 and about 15 nucleotides long; and (c) a third region suitable for use as a sequencing primer (e.g., a next generation sequencing (NGS) primer), and a second oligonucleotide that comprises, in 5' to 3' order, (d) a first region that is substantially identical to the third region of the first oligonucleotide; and (e) a second region that is suitable for use as a polymerase chain reaction (PCR) primer, wherein the third region of the first oligonucleotide and the first region of the second oligonucleotide have a melting temperature (Tm) that is at least about 5° C. higher than the Tm of the second region of the second oligonucleotide, and wherein the total length of the spacer and the first and second regions of the second oligonucleotide is at least about 45 nucleotides (nt) long.

In some aspects, the first oligonucleotide is not longer than about 80 nt, 90 nt, 100 nt, 110 nt, or 120 nt. In some aspects, the second oligonucleotide is not longer than about 50 nt, 60 nt, 70 nt or 80 nt. In some aspects, the Tm of the third region of the first oligonucleotide and the first region of the second oligonucleotide is between about 65° C. and about 75° C. In some aspects, the Tm of the second region of the second oligonucleotide is between about 55° C. and about 65° C.

In some aspects, the first region of the first oligonucleotide is selected from Table 1. In some aspects, the third region of the first oligonucleotide and the first region of the second oligonucleotide are selected from Table 2.

In some aspects, the composition further comprises a third oligonucleotide that comprises, in 5' to 3' order, (a) a first region suitable for use as a sequencing primer (e.g., a Sanger sequencing primer); (b) a spacer that is between about 5 and about 15 nucleotides long; and (c) a third region suitable for use as a sequencing primer (e.g., a next generation sequencing (NGS) primer), and a fourth oligonucleotide that comprises, in 5' to 3' order, (d) a first region that is substantially identical to the third region of the third oligonucleotide; and (e) a second region that is suitable for use as a polymerase chain reaction (PCR) primer, wherein the third region of the third oligonucleotide and the first region of the fourth oligonucleotide have a melting temperature (Tm) that is at least about 5° C. higher than the Tm of the second region of the fourth oligonucleotide, wherein the total length of the spacer of the third oligonucleotide and the first and second regions of the fourth oligonucleotide is at least about 45 nucleotides (nt) long, and wherein the first region of the first oligonucleotide is substantially different from the first region of the third oligonucleotide and the first region of the second oligonucleotide is substantially different from the first region of the fourth oligonucleotide.

In some aspects, the second region of the second oligonucleotide and the second region of the fourth oligonucleotide are suitable for amplifying a human genomic sequence.

Also provided, in one embodiment, is an oligonucleotide comprising, in 5' to 3' order: (a) a first region selected from the nucleic acid sequences of Table 1; (b) a spacer that is between about 5 and about 15 nucleotides long; and (c) a third region selected from the nucleic acid sequences of Table 2. In some aspects, the oligonucleotide comprises a sequence of
GTAAAACGACGGCCAGTATTTAGGTGACACTATA-
GACACTGACGACATGGTTCT ACA (SEQ ID NO: 9) or
AACAGCTATGACCATGCAGTCAAGTAACAACCGC-
GATACGGTAGCAGAGACTTG GTCT (SEQ ID NO: 10).

In another embodiment, provided is a method for amplifying a nucleotide sequence, comprising: (i) incubating a target nucleotide template with a first and third oligonucleotides each comprising, in 5' to 3' order, (a) a first region suitable for use as a sequencing primer (e.g., a Sanger sequencing primer); (b) a spacer that is between about 5 and about 15 nucleotides long; and (c) a third region suitable for use as a sequencing primer (e.g., a next generation sequencing (NGS) primer), and a second and fourth oligonucleotides comprising, in 5' to 3' order, (d) first regions that are substantially identical to the third region of the first or third oligonucleotide, respectively; and (e) second regions which, in combination, suitable for amplifying the target nucleotide template as a pair of polymerase chain reaction (PCR) primers, wherein the third regions of the first and third oligonucleotides and the first regions of the second and fourth oligonucleotides have a melting temperature (Tm) that is at least about 5° C. higher than the Tm of the second regions of the second and fourth oligonucleotide, and wherein the total length of the spacer of the first oligonucleotide and the first and second regions of the second oligonucleotide is at least about 45 nucleotides (nt) long and the total length of the spacer of the third oligonucleotide and the first and second regions of the fourth oligonucleotide is at least about 45 nucleotides (nt) long, and wherein the first region of the first oligonucleotide is substantially different from the first region of the third oligonucleotide and the first region of the second oligonucleotide is substantially different from the first region of the fourth oligonucleotide; (ii) performing a plurality of PCR cycles with a first annealing temperature (Ta) suitable for amplification using the second regions of the second and fourth oligonucleotides as primers; and (iii) performing a plurality of PCR cycles with a second annealing temperature (Ta) suitable for amplification using the third regions of the first and third oligonucleotides as primers.

In some aspects, the first regions of the first and third oligonucleotides are selected from Table 1. In some aspects, the first regions of the third and fourth oligonucleotides are selected from Table 2.

In some aspects, the first Ta is between about 53° C. and about 57° C. In some aspects, the second Ta is between about 59° C. and about 63° C.

In some aspects, the ratios of concentrations of the first oligonucleotide to the second oligonucleotide and the third oligonucleotide to the fourth oligonucleotide are less than about 1:1.

Also provided, in one embodiment, is a composition or kit, comprising a first and second oligonucleotides each comprising, in 5' to 3' order, (a) a first region suitable for use as a sequencing primer (e.g., a Sanger sequencing primer); (b) a spacer that is between about 5 and about 15 nucleotides long; and (c) a third region suitable for use as a sequencing primer (e.g., a next generation sequencing (NGS) primer), wherein the first regions of the first and second oligonucleotides are substantially different and the third regions of the first and second oligonucleotides are substantially different.

In some aspects, the first regions of the first and second oligonucleotides are selected from Table 1. In some aspects, the third regions of the first and second oligonucleotides are selected from Table 2.

With reference to FIGS. 1 and 2, one embodiment of the present disclosure provides an amplification method that entails PCR amplification with two pairs of primers.

An inner primer set is used for generating an amplicon for a first round of sequencing, such as a Next Generation Sequencing (NGS). Each of the inner primers includes, from 5' to 3', a first region suitable for use as primer for sequencing and a second region that is specific for a target nucleotide sequence. The sequencing primer regions are referred to as Adaptors A (for forward sequencing) and B (for reverse sequencing), as shown in FIG. 2. Also as shown in FIG. 2, the second regions are referred to as gene-specific primers forward (GSP F) and reverse (GSP R).

Such inner primer sets are similar to those used in NGS, in which the GSPs serve as primers for the target-specific PCR amplifications, and the Adaptors are then used for sequencing the amplicons.

Unlike the inner primer set, the outer primer set does not include any sequence that is specific to the target nucleotide sequence. At the 3' end, each of the outer primers includes a region (third region) that is identical or substantially identical to Adaptor A or B. Then, at the 5' end, each of the outer primers includes a first region that is suitable for initiation a second round of sequencing (e.g., Sanger sequencing). Accordingly, these first regions can be referred to as "Sanger primer regions," without being limited to primers useful for Sanger sequencing.

A nucleic acid sequence being "substantially identical" to a reference nucleic acid, as used herein, means that the nucleic acid is able to hybridize, under suitable or designated hybridizing conditions, to the complementary strand of the reference nucleic acid. In some aspects, the nucleic has at most 1, or 2 or 3 nucleotide mismatches or deletion/insertion from the reference nucleic acid.

Therefore, a first cycle of amplification with the inner primer set will generate an amplicon that includes, at both ends, the inner primer sequences. Such an amplicon, therefore, can subsequently undergo PCR amplification with the outer primer set as well, by virtue of the sequence identity between the 3' ends of the outer primers and the 5' ends of the inner primers. Which primer set is used in the subsequent PCR cycles can depend on the availability of the primers as well as factors such as annealing temperature.

At the end of the PCR amplification, therefore, at least two types of amplicons are generated. One of them includes both inner primers at the ends, and the other includes both outer primers at the ends. The later one is suitable for sequencing with either the Sanger primers regions or the Adaptor regions. Accordingly, the above amplification methods can generate amplicons suitable for two separate rounds and types of sequencing. One exemplary use of such an amplicon is for a NGS sequencing followed by a Sanger sequencing validation.

It is further discovered that the inner and outer primer sets can be designed to favor PCR amplification with either set of the primers while needed. For instance, in one embodiment, the Adaptors can be nucleic acid sequences that have a relatively high melting temperature ($T_m$) and the target-specific primers can have a relatively lower $T_m$. As such, when the annealing temperature ($T_a$) is low, the amplification preferentially utilizes the inner primers. By the same token, when the $T_a$ is higher, the amplification preferentially utilizes the outer primers.

For instance, if the Adaptors' $T_m$ is around 70° C. and the GSPs' $T_m$ is around 60° C., a $T_a$ of about 55° C. will strongly favor the GSPs and a $T_a$ of about 62° C. will strongly favor the Adaptors. In accordance with such a design, the present disclosure provides a PCR reaction in which the amplification is carried out, for a number of cycles, with a lower $T_a$, to ensure that a sufficient number of amplicons is generated, having the inner primers at both ends. Subsequently, cycles with increased $T_a$ will enable such amplicons to undergo amplification with the outer primers.

In some aspects, the Adaptors have a $T_m$ that is at least about 5° C., or 6° C., 7° C., 8° C., 9° C., 10° C., 11° C., 12° C., 13° C., 14° C., or 15° C. higher than the $T_m$ of the GSPs. In some aspects, the PCR amplifications are carried out first in a number of cycles with a $T_a$ between about 53° C. and about 57° C., or between about 54° C. and about 56° C., or at about 55° C. Subsequently, the PCR amplifications are carried out in a number of cycles with a $T_a$ between about 59° C. and about 65° C., or between about 60° C. and about 64° C., or between about 61° C. and about 63° C., or at about 62° C.

In some aspects, the PCR is carried out under the lower $T_a$ for at least 10 cycles. In some aspects, the PCR is then carried out under the higher $T_a$ for at least about 20 cycles.

In some aspects, the outer primers further include a spacer region between the Sanger primer region and the Adaptors. In one aspect, the total length of the spacer, the Adaptor and the GSP is at least about 50 nucleotides such that the Sanger sequencing can effectively begin at the target sequence right next to the GSP. This is because Sanger sequencing generally starts at about 50 nt from the primer site. In some aspects, the total length is at least about 55 nt, 60 nt, or 65 nt. In some aspects, the spacer is between about 5 nt and about 15 nt long. In one aspect, the spacer is at least about 6, or 7, 8, 9, 10, 11, or 12 nt long.

The present technology, therefore, is able to provide primer sets suitable for amplify multiple target nucleic acid sequences (using target or gene-specific primers), using the present methods, with the resulting amplicons suitable for two types of sequencing. In this respect, it is noted that methods and packages/kits are also provided, employing multiple oligonucleotide sets as described here. These multiple oligonucleotide sets each includes different PCR primers targeting different nucleic acid sequences or genes of interest, but includes the same Sanger and NGS sequencing primers. In some aspects, the methods or packages/kits include at least 2, or 3, or 4, or 5, or 10, or 20, or 30, or 40 or 50, or 100 such oligonucleotide sets.

Methods are known in the art to design primer sequences for sequencing, such as Sanger sequencing. In one aspect, the Sanger sequencing primer region is a sequence selected from Table 1. In another aspect, the Adaptor region is a sequence selected from Table 2.

TABLE 1

Exemplary Universal Primers for Sanger Sequencing

| Primer | Sequence(5' -> 3') | Size (nt) | SEQ ID NO. |
|---|---|---|---|
| M13F | GTAAAACGACGGCCAGT | 17 | 1 |
| M13R | AACAGCTATGACCATG | 16 | 2 |
| M13-26REV | CAGGAAACAGCTATGAC | 17 | 11 |
| M13-40FOR | GTTTTCCCAGTCACGAC | 17 | 12 |
| M13-48REV | CGGATAACAATTTCACACAG | 20 | 13 |
| M13F-20 | GTAAAACGACGGCCAGTG | 18 | 14 |
| 1629DWN | CTGTAAATCAACAACGCACAG | 21 | 15 |
| 3AOX1 | <GCAAATGGCATTCTGACATCC | 21 | 16 |
| 5AOX1< | GACTGGTTCCAATTGACAAGC | 21 | 17 |
| A-FACTOR | TACTATTGCCAGCATTGCTGC | 21 | 18 |
| ACYCDUETUP1 | GGATCTCGACGCTCTCCCT | 19 | 19 |
| ATTB1 | GTTTGTACAAAAAAGCAGGC | 20 | 20 |
| ATTB2 | CCACTTTGTACAAGAAAGCTGGGT | 24 | 21 |
| ATTL1 | CGCGTTAACGCTAGCATGGATCTC | 24 | 22 |
| ATTL2 | CATCAGAGATTTTGAGACAC | 20 | 23 |
| BD-FOR | TCATCGGAAGAGAGTAG | 17 | 24 |
| BD-REV | CGTTTTAAAACCTAAGAGTCA | 21 | 25 |
| BGHR2 | GGGTCAAGGAAGGCACG | 17 | 26 |
| BGHREV | TAGAAGGCACAGTCGAGG | 18 | 27 |
| CMV-FOR | CGCAAATGGGCGGTAGGCGTG | 21 | 28 |
| DUETDOWN1 | GATTATGCGGCCGTGTACAA | 20 | 29 |
| EF-1-ALPHA | TCAAGCCTCAGACAGTGGTTC | 21 | 30 |
| EGFP-C-FOR | CATGGTCCTGCTGGAGTTCGTG | 22 | 31 |

TABLE 1-continued

Exemplary Universal Primers for Sanger Sequencing

| Primer | Sequence(5' -> 3') | Size (nt) | SEQ ID NO. |
| --- | --- | --- | --- |
| EGFP-C-REV | GTTCAGGGGAGGTGTG | 17 | 32 |
| EGFP-N | CGTCGCCGTCCAGCTCGACCAG | 22 | 33 |
| GAL1-FORWARD | ATTTTCGGTTTGTATTACTTC | 21 | 34 |
| GAL4AD | TACCACTACAATGGATG | 17 | 35 |
| GL-PRIMER1 | TGTATCTTATGGTACTGTAACTG | 23 | 36 |
| GL-PRIMER2 | CTTTATGTTTTGGCGTCTTCCA | 23 | 37 |
| ITS1 | TCCGTAGGTGAACCTGCGG | 19 | 38 |
| ITS4 | TCCTCCGCTTATTGATATGC | 20 | 39 |
| ITSL | TCGTAACAAGGTTTCCGTAGGTG | 23 | 40 |
| KS | TCGAGGTCGACGGTATC | 17 | 41 |
| MAL-E | GGTCGTCAGACTGTCGATGAAGCC | 24 | 42 |
| OP1E2FOR | CGCAACGATCTGGTAAACAC | 20 | 43 |
| OP1E2REV | GACAATACAAACTAAGATTTAGCT | 24 | 44 |
| PBADF | ATGCCATAGCATTTTTATCC | 20 | 45 |
| PBADR | GATTTAATCTGTATCAGG | 18 | 46 |
| PCEP-FOR | AGAGCTCGTTTAGTGAACCG | 20 | 47 |
| PCEP-REV | GTGGTTTGTCCAAACTCATC | 20 | 48 |
| PDON-R | GTAACATCAGAGATTTTGAGACAC | 24 | 49 |
| PENTR-1A-FOR | GTTTCTACAAACTCTTCCTG | 20 | 50 |
| PET-UPSTREAM | ATGCGTCCGGCGTAGA | 16 | 51 |
| PETBLUEDOWN | GTTAAATTGCTAACGCAGTCA | 21 | 52 |
| PETBLUEUP | TCACGACGTTGTAAAACGAC | 20 | 53 |
| PFASTBAC-F | CATACCGTCCCACCATCG | 18 | 54 |
| PFASTBAC-R | ATCCTCTAGTACTTCTCGAC | 20 | 55 |
| PGEX3P | CCGGGAGCTGCATGTGTCAGAGG | 23 | 56 |
| PGEX5FUPSTM | TGGACCCAATGTGCCTG | 17 | 57 |
| PGEX5P | GGGCTGGCAAGCCACGTTTGGTG | 23 | 58 |
| PINDIGO-REV | CTCGTATGTTGTGTGGAATTGTGAGC | 26 | 59 |
| PIRES-REV | CATATAGACAAACGCACAC | 19 | 60 |
| PJG4-5-FOR | GATGCCTCCTACCCTTATGATGTGCC | 26 | 61 |
| POLYTV | TTTTTTTTTTTTTTTTTTTTTTTV | 24 | 62 |
| PQE-FOR | CCCGAAAAGTGCCACCTG | 18 | 63 |
| PQE-REV | GTTCTGAGGTCATTACTG | 18 | 64 |
| PREP-FOR | GCTCGATACAATAAACGCC | 19 | 65 |
| PSHUTCMV-FOR | GGTCTATATAAGCAGAGCTG | 20 | 66 |
| PSHUTCMV-REV | GTGGTATGGCTGATTATGATCAG | 23 | 67 |
| PTRC-99A-FOR | GACATCATAACGGTTCTG | 18 | 68 |
| PTRC-99A-REV | CTGAGTTCGGCATGGGG | 17 | 69 |
| PTRCHIS-F | GAGGTATATATTAATGTATCG | 21 | 70 |
| PTRCHIS-R | GATTTAATCTGTATCAGG | 18 | 71 |
| RVPRIMER3 | CTAGCAAAATAGGCTGTCCC | 20 | 72 |
| RVPRIMER4 | GACGATAGTCATGCCCCGCG | 20 | 73 |
| S.TAG | CGAACGCCAGCACATGGACA | 20 | 74 |
| SK-PRIMER | CGCTCTAGAACTAGTGGATC | 20 | 75 |
| SP6 | ATTTAGGTGACACTATAG | 18 | 76 |
| T3P | ATTAACCCTCACTAAAGGGA | 20 | 77 |
| T7-REV | TAGTTATTGCTCAGCGGTGG | 20 | 78 |
| T7-SELECTDWN | AACCCCTCAAGACCCGTTTA | 20 | 79 |
| T7P | TAATACGACTCACTATAGGG | 20 | 80 |
| T7TERM | CTAGTTATTGCTCAGCGG | 18 | 81 |
| TRX-FORWARD | TTCCTCGACGCTAACCTG | 18 | 82 |
| U-19 | GTTTTCCCAGTCACGACGT | 19 | 83 |

TABLE 2

Exemplary Next Generation Sequencing Primers

| Primer | Sequence(5' -> 3') | Size (nt) | SEQ ID NO. |
| --- | --- | --- | --- |
| Adaptor A | ACACTGACGACATGGTTCTACA | 22 | 7 |
| Adaptor B | TACGGTAGCAGAGACTTGGTCT | 22 | 8 |

In some embodiments, the inner and outer primer sets are present in relative ratios of greater than about 1:1. In one embodiment, the inner and out primer sets have a ratio that is at about 2.5:1, or between about 2:1 and 3:1, or between about 1.5:1 and 4:1, or between about 1:1 and 5:1.

In one embodiment, an outer primer is provided that comprises, in 5' to 3' order (a) a 5' sequence derived from M13 sequencing primers, wherein the sequence comprises GTAAAACGACGGCCAGT (SEQ ID NO: 1) or AACAGCTATGACCATG (SEQ ID NO: 2); (b) a spacer comprising at least 10 nucleotides, and (c) a 3' adapter that is substantially identical to the 5' region of primers used in the next generation sequencing amplification. In related embodiments, the spacer comprises a sequence selected from ATTTAGGTGACACTATAG (SEQ ID NO: 3) or CAGTCAAGTAACAACCGCGA (SEQ ID NO: 4). For example, the oligonucleotide primer may comprise a sequence selected from GTAAAACGACGGCCAGTATT-TAGGTGACAC TATAG (SEQ ID NO: 5) or AACAGC- TATGACCATGCAGTCAAGTAACAACCGCGA (SEQ ID NO: 6). In further embodiments, the adapter comprises a sequence selected from ACACTGACGACA TGGTTCTACA (SEQ ID NO: 7) or TACGGTAGCAGAGACTT GGTCT (SEQ ID NO: 8). Thus, in an exemplary embodiment, the oligonucleotide primer comprises a sequence selected from GTAAAACGACGGCCAGTATTTAGGTGACACTA TAGACACTGACGAC ATGGTTCTACA (SEQ ID NO: 9) or AACAGCTATGACC ATGCAGTCAAGTAACAA CCGCGATACGGTAGCAGAGACTTGGTCT (SEQ ID NO: 10).

In one embodiment, the invention is a method for generating an amplicon for next generation sequencing with subsequent validation, for at least one region of interest, comprising (a) adding, to a sample of DNA,
(i) a first primer set specific for the region of interest, consisting of two primers each comprising a 5' region encoding an adapter and a 3' region specific for the region of interest, wherein the first primer set binds with a T$_m$ of approximately 60° C. immediately upstream and downstream of the region of interest;
(ii) a second primer set consisting of two primers each of which comprises
(A) a 5' sequence selected from GTAAAACGACGGCCAGT (SEQ ID NO: 1) or AACAGCTATGACCATG (SEQ ID NO: 2);
(B) a spacer comprising at least 10 nucleotides
(C) a 3' adapter that is substantially identical to the adapter region, wherein the adapter has a T$_m$ of approximately 55° C., and wherein the second primer set has a Tm of at least 70° C.; followed by thermocycling for about 10 cycles with 55° C. annealing and about 30 cycles at 60-62° C. annealing. For example, thermocycling may comprise (a) heating to 95° C.; (b) extending for about 10 cycles of (i) 95° C. (ii) 55° C. (ii) 72° C.; and (c) extending for about 30 cycles of (i) 95° C. (ii) 60-62° C. (ii) 72° C. In some embodiments, an additional extension step is added, such as 72° C. for 15 minutes. In such methods, the ratio of the first primer set and the second primer set may affect the efficiency and specificity of the amplification.

The amplicons generated may then be subject to sequencing, such as by the addition of a primer selected from GTAAAACGACGGCCAGT (SEQ ID NO: 1) and AACAGCTATGACCATG (SEQ ID NO: 2); extending in the presence of dNTPs and dye-labelled dNTPs to generate a population of labeled nucleotides; and resolving the population of labeled nucleotides.

The invention also includes compositions and kits. In one aspect, the composition or kit includes a forward inner primer and a forward outer primer as described. In one aspect, the composition or kit includes a forward outer primer and a reverse outer primer as described. In another aspect, the composition or kit includes an inner primer set and an outer primer set as described.

In one embodiment, the invention is a kit for the amplification and sequencing of a region of interest, comprising (i) a first primer set specific for the region of interest, consisting of two primers each comprising a 5' region encoding an adapter and a 3' region specific for the region of interest, wherein the first primer set binds with a Tm of approximately 60° C. immediately upstream and downstream of the region of interest; (ii) a second primer set consisting of two primers each of which comprises (A) a 5' sequence selected from GTAAAACGACGGCCAGT (SEQ ID NO: 1) or AACAGCTATGACCATG (SEQ ID NO: 2); (B) a spacer comprising at least 10 nucleotides (C) a 3' adapter that is substantially identical to the adapter region, wherein the adapter has a Tm of approximately 55° C., and wherein the second primer set has a Tm of at least 70° C. In an exemplary embodiment, the second primer set comprises: GTAAAACGACGGCCAGTATTTAGGTGACACTATAGACACTGACGACATGGTTCT ACA (SEQ ID NO: 9); and AACAGCTATGACCATGCAGTCAAGTAACAACCGCGATA CGGTAGCAGAGACTTGGTCT (SEQ ID NO: 10). Kits of the invention may further comprise suitable buffers and controls.

DETAILED DESCRIPTION

Figure 1:
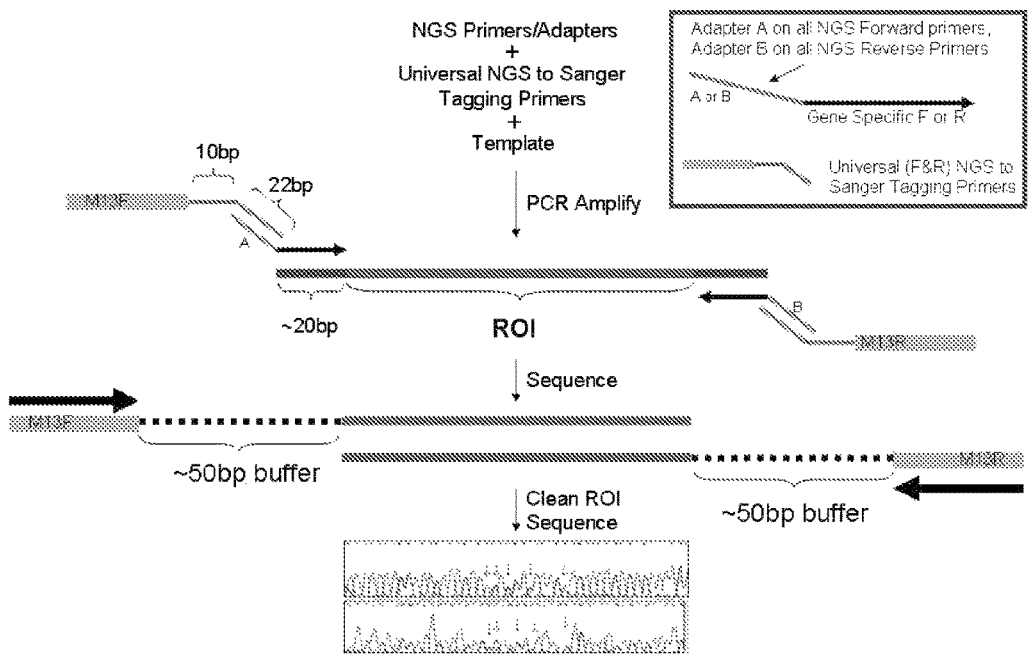
FIG. 1. Simultaneous nested PCR allows addition of Sanger sequencing priming sites and extension linkers by universal priming of adapter sequences.

Described herein are primers, methods, reagents and kits for independently validating the DNA sequence of an amplicon that was, or will be, subjected to next-generation sequencing.

To facilitate an understanding of the present invention, a number of terms and phrases are defined below.

As used herein, unless otherwise stated, the singular forms "a," "an," and "the" also include the plural. Thus, for example, a reference to "an oligonucleotide" includes a plurality of oligonucleotide molecules, a reference to label is a reference to one or more labels, a reference to probe is a reference to one or more probes, and a reference to "a nucleic acid" is a reference to one or more polynucleotides.

As used herein, unless indicated otherwise, when referring to a numerical value, the term "about" means plus or minus 10% of the enumerated value.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product," also known as an "amplicon." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.,* 29(11):E54-E54, 2001; Hafner et al., *Biotechniques,* 30(4):852-56, 858, 860, 2001; Zhong et al., *Biotechniques,* 30(4):852-6, 858, 860, 2001.

A key feature of PCR is "thermocycling" which, in the present context, comprises repeated cycling through at least three different temperatures: (1) melting/denaturation, typically at 95° C. (2) annealing of a primer to the target DNA at a temperature determined by the melting point (Tm) of the region of homology between the primer and the target and (3) extension at a temperature dependent on the polymerase, most commonly 72° C. These three temperatures are then repeated numerous times. Thermocycling protocols typically also include a first period of extended denaturation, and end on an extended period of extension.

The Tm of a primer varies according to the length, G+C content, and the buffer conditions, among other factors. As used herein, Tm refers to that in the buffer used for the reaction of interest.

As used herein, the term "detecting" refers to observing a signal from a detectable label to indicate the presence of a target. More specifically, detecting is used in the context of detecting a specific sequence.

The terms "complement," "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association." For example, for the sequence 5'-A-G-T-3' is complementary to the sequence 3'-T-C-A-5'. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides.

The terms "identity" and "identical" refer to a degree of identity between sequences. There may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated," "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable moieties.

The term "Nested polymerase chain reaction" is a modification of polymerase chain reaction which, in the present context, is performed to add sequences to an amplicon. Nested polymerase chain reaction involves two sets of primers, used in two successive runs of polymerase chain reaction, the second set intended to amplify the target from the first run product.

As used herein, the term "oligonucleotide" refers to a short polymer composed of deoxyribonucleotides, ribonucleotides, or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of DNA. A "reverse primer" is complementary to the sense-strand of DNA.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

The term "adapter" refers to a short, chemically synthesized, DNA molecule which is used to link the ends of two other DNA molecules, or to provide a common template for other manipulations, such as sequencing. In the present context, an adapter is used in next-generation sequencing as the basis for sequencing.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

As used herein, an oligonucleotide is "specific" for a nucleic if it is capable of hybridizing to the target of interest and not substantially hybridizing to nucleic acids which are not of interest. High levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art (e.g., BLAST).

The term "region of interest" refers to a region of a nucleic acid to be sequenced.

The term "transcript," when referring to a target nucleic acid, refers to any nucleic acid transcript, including mRNA, pre-mRNA, and snRNA, and synthetic representations thereof such as cDNA.

The term "biological sample" as used herein refers to a sample containing nucleic acids of interest. A biological sample may comprise clinical samples (i.e., obtained directly from a patient) or isolated nucleic acids and may be cellular or acellular fluids and/or tissue (e.g., biopsy) samples. In some embodiments, a sample is obtained from a tissue or bodily fluid collected from a subject. Sample sources include, but are not limited to, sputum (processed or unprocessed), bronchial alveolar lavage (BAL), bronchial wash (BW), whole blood or isolated blood cells of any type (e.g., lymphocytes), bodily fluids, cerebrospinal fluid (CSF), urine, plasma, serum, or tissue (e.g., biopsy material). Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like. In the present context the biological sample preferably is blood, serum or plasma. The term "patient sample" as used herein refers to a sample obtained from a human seeking diagnosis and/or treatment of a disease, especially prostate disease.

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who possesses, or is suspected to possess, a genetic polymorphism of interest.

Amplification of Nucleic Acids.

Nucleic acid samples or target nucleic acids may be amplified by various methods known to the skilled artisan. In suitable embodiments, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

In one embodiment, the target nucleic acids are amplified in a multiplex amplification or nested reaction. If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IC) can be included in the sample, utilizing oligonucleotide primers and/or probes.

Detection of Amplified Nucleic Acids.

Amplification of nucleic acids can be detected by methods known in the art such as gel electrophoresis, column chromatography, hybridization with a probe, sequencing, melting curve analysis, or "real-time" detection.

General Overview of the Technology.

Next generation sequencing methods are fast and low cost compared to older technologies. However, in a clinical diagnostic setting, accuracy is extremely important. Therefore, following a next-generation sequencing protocol, such as Ion Torrent, any clinically relevant results need to be confirmed and validated by an independent and more reliable technique. Thus, when a region of interest is amplified and sequenced with the aid of a set of first primers, there is required a way to verify the sequencing results.

Applicants have met this need by providing a second set of primers that extend an amplicon of interest to add well understood and characterized "universal" primers and a spacer region. The resulting amplicon can then be sequenced with a universal primer. The spacer region ensures that highly accurate sequencing, which typically starts 50 nucleotides from the primer, encompasses the region of interest.

The amplification of a region of interest with the second set of primers can be done in a separate reaction. For example, the region of interest can be amplified with the first set of primers and sequences with next generation techniques. After identifying an amplicon of interest, the amplicon can then be further amplified and tagged with the second set of primers, and resequenced.

Preferably, however, amplification with the first and second set of primers occurs using nested PCR to result in an amplicon that is first sequenced with next generation technology and then with older technology. This approach avoids errors from repeated amplification.

EXAMPLES

Example 1: Proof of Concept with PIK3CA Primers

We developed a primer set for Universal Sanger Sequencing from Next Gen Sequencing amplicons.

This design takes advantage of the universal adapters that are incorporated into each amplicon of a Next Gen Sequencing library. For example, Ion Torrent PGM incorporates the forward (adapter A) and reverse (adapter B) shown in Table 3. Primers for each amplicon making up the library are tagged with adapter A on the 5' region of the forward primer and adapter B on the 5' region of the reverse primer.

TABLE 3

| Ion Torrent PGM adapters | |
|---|---|
| Adapter | 5' --> 3' Sequence |
| Adapter A | ACACTGACGACATGGTTCTACA (SEQ ID NO: 7) |
| Adapter B | TACGGTAGCAGAGACTTGGTCT (SEQ ID NO: 8) |

The universal Sanger sequencing primer set (Table 4) utilizes these adapter sequences as the priming sites and includes an extension linker as well as M13F and M13R for sequencing (FIG. 1). The M13 sequencing sites and extension linkers were synthesized onto the product during a simultaneous nested PCR strategy. Briefly, the gene specific primers and Universal Sanger sequencing primers were added to the same reaction to obtain full length amplicon. The purpose of the extension linkers was to serve as a space buffer to allow clean sequence reads, which generally begins ~50 bp from the priming site, to begin near the start of the region of interest.

TABLE 4

Universal Sanger Sequencing Primers

NG2SANG-F: M13F-SP6-AdA
(M13F = 17; Entire oligo = 57)
(SEQ ID NO: 9)
5'-GTAAAACGACGGCCAGT ATTTAGGTGACACTATAG ACACTGACGACATGGTTCTACA-3'

NG2SANG-R: M13R-LucF-AdB
(M13R = 16; Entire oligo = 58)
(SEQ ID NO: 10)
5'-AACAGCTATGACCATG CAGTCAAGTAACAACCGCGA TACGGTAGCAGAGACTTGGTCT-3'

Figure 2:
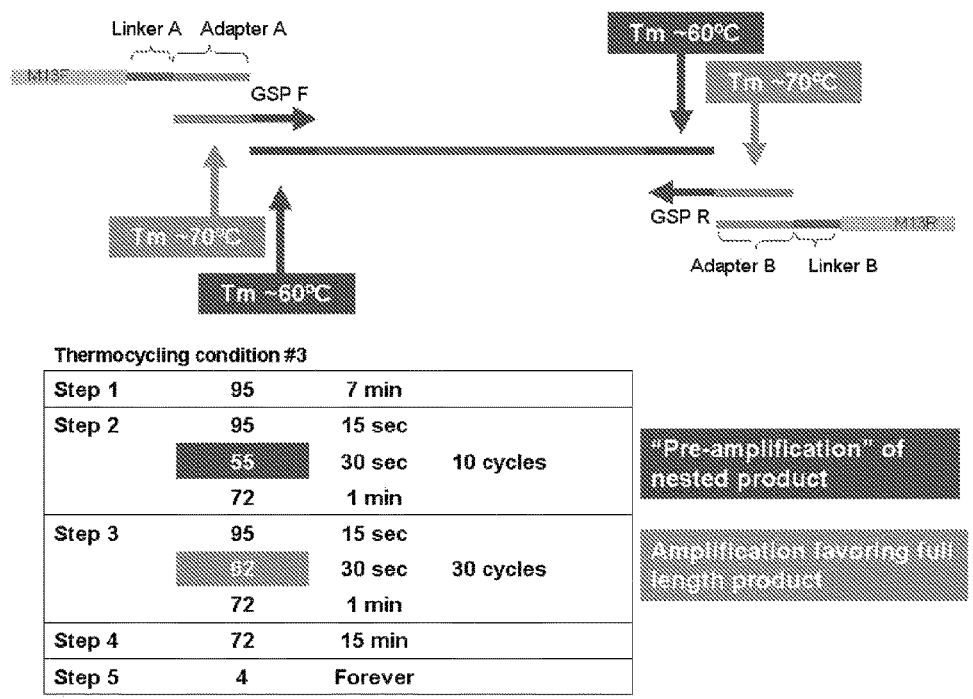
FIG. 2. Thermocycling parameters favoring generation of full length amplicon.

One caveat with simultaneous nested PCR is that shorter products are generally favored in a multiplex PCR reaction. Therefore, the nested product is likely to be synthesized in far excess of the full length product containing sequencing sites. However, by altering the thermocycling conditions to favor the full length product, we were able to significantly increase the yield. Since the gene specific sites all contain melting temperatures (Tm) around 60° C. and the adapter sites have Tm closer to 70° C., we ran the first 10 cycles with an annealing temperature of 55° C. followed by 30 cycles at 62° C. (FIG. 2). The increased annealing temperature in the last 30 cycles favors the binding of the adapter-specific (outer) primers since the gene-specific (inner) primers are much less likely to bind at this elevated temperature.

Figure 3:
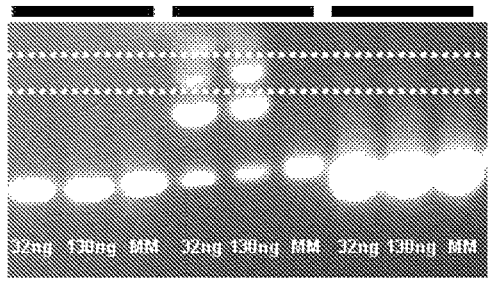
FIG. 3A-3C. Results from varying thermocycling and primer ratio parameters. P, PIK3CA-specific inner primers; N, NGS universal outer primers.
Figure 3:
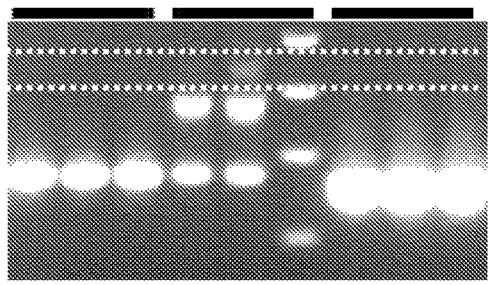
Figure 3:
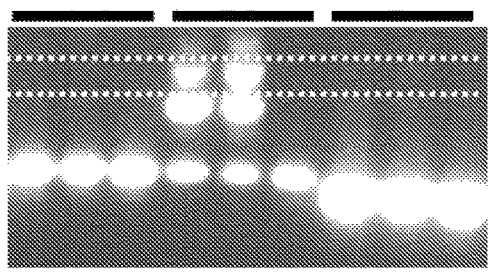

These thermocycling conditions were compared to standard thermocycling (Thermocycling condition #1) as well as thermocycling indicated for AccessArray Barcode addition (Thermocycling condition #2) (FIG. 3). Various Inner:Outer (P:N; P, PIK3CA-specific inner primers; N, NGS universal outer primers) primer ratios were also evaluated for optimal generation of full length product (1:10, 2.5:1, 1:4). Results of these experiments indicate that our modified thermocycling conditions and an Inner:Outer primer ratio of 2.5:1 yielded the maximum full length product (FIG. 3).

Figure 5:
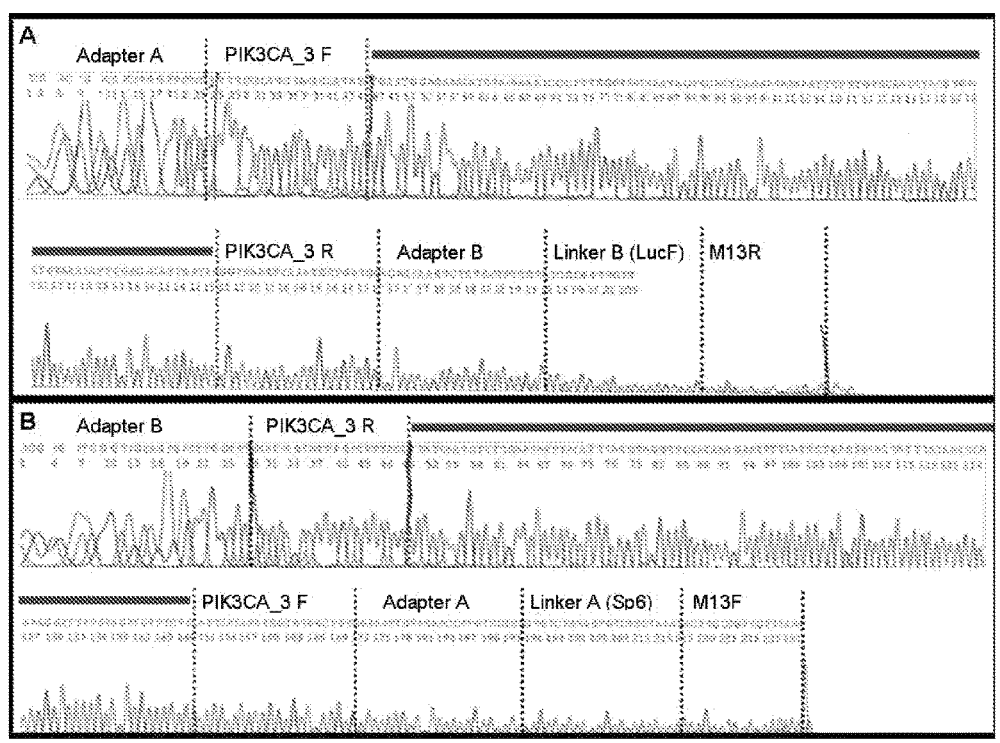
FIG. 5A-5B. Sequencing results from purified full length PIK3CA_3 product. Forward sequence (A), and reverse sequence (B) both contain clean, interpretable sequence (SEQ ID NO: 11) covering the region of interest (blue bar).

The resulting PCR product was purified from an agarose gel, selecting for the full length product. BigDye Sequencing was performed using M13 forward and reverse sequencing primers. The resulting forward (FIG. 5A) and reverse (FIG. 5A) sequences yielded clean, interpretable results covering the entire region of interest.

Figure 4:
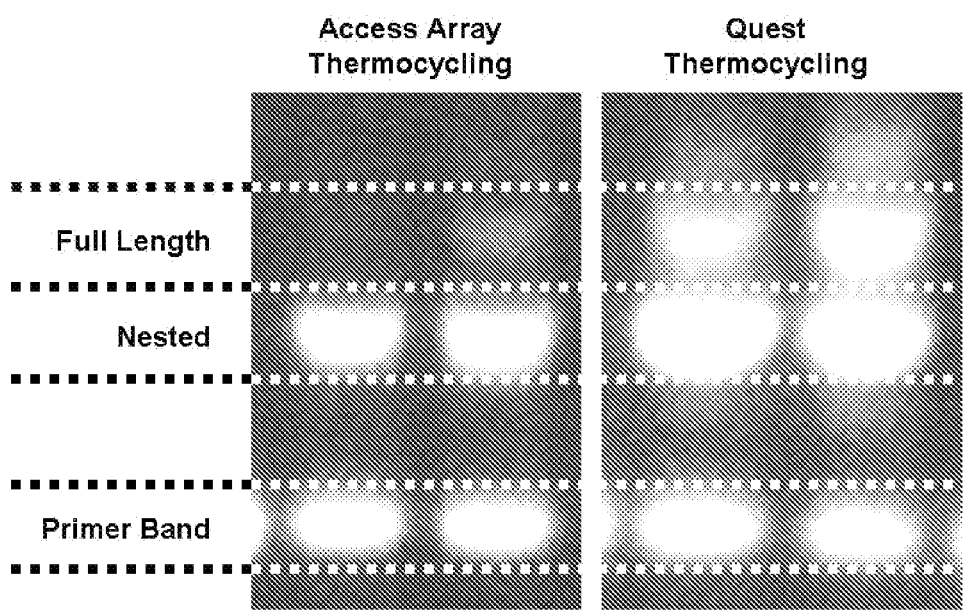
FIG. 4. Comparison of AccessArray thermocycling conditions to the Quest modified conditions favoring full length amplicon production (thermocycling condition #3). All reaction conditions were identical with only the thermocycling parameters changed.

This design allows for the same sequencing primers to be added to any amplicon primer set containing adapters A and B to allow for rapid validation of any observed mutation in the library. Notably, FIG. 4 shows the side-by-side result from our final conditions as compared to the Fluidigm recommended conditions used for addition of Barcodes in the AccessArray platform. Since the adapter sequences are identical, it is expected that the efficiency of the reactions would be similar. Indeed, the present method resulted in much higher yield of the full length product (FIG. 4).

Other Embodiments

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising," "including," containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Other embodiments are set forth within the following claims.

What is claimed is:

1. A composition comprising:
   a first oligonucleotide that comprises, in 5' to 3' order,
     (a) a first region suitable for use as a Sanger sequencing primer;
     (b) a spacer that is between about 5 and about 15 nucleotides long; and
     (c) a third region suitable for use as a next generation sequencing (NGS) primer, and
   a second oligonucleotide that comprises, in 5' to 3' order,
     (a) a first region that is substantially identical to the third region of the first oligonucleotide; and
     (b) a second region that is suitable for use as a polymerase chain reaction (PCR) primer to amplify a target nucleotide sequence,
   wherein the third region of the first oligonucleotide and the first region of the second oligonucleotide have a melting temperature ($T_m$) that is at least about 5° C. higher than the $T_m$ of the second region of the second oligonucleotide,
   wherein the total length of the spacer and the first and second regions of the second oligonucleotide is at least about 45 nucleotides (nt) long,
   wherein the third region of the first oligonucleotide and the first region of the second oligonucleotide are selected from Table 2, and
   wherein the third region of the first oligonucleotide and the first region of the second oligonucleotide do not include any sequence that is specific to the target nucleotide sequence.

2. The composition of claim 1, wherein the first oligonucleotide is not longer than about 100 nt.

3. The composition of claim 1, wherein the second oligonucleotide is not longer than about 60 nt.

4. The composition of claim 1, wherein the $T_m$ of the third region of the first oligonucleotide and the first region of the second oligonucleotide is between about 65° C. and about 75° C.

5. The composition of claim 1, wherein the $T_m$ of the second region of the second oligonucleotide is between about 55° C. and about 65° C.

6. The composition of claim 1, wherein the first region of the first oligonucleotide is selected from Table 1.

7. The composition of claim 1, further comprising:
   a third oligonucleotide that comprises, in 5' to 3' order,
     (a) a first region suitable for use as a Sanger sequencing primer;
     (b) a spacer that is between about 5 and about 15 nucleotides long; and
     (c) a third region suitable for use as a next generation sequencing (NGS) primer, and
   a fourth oligonucleotide that comprises, in 5' to 3' order,
     (a) a first region that is substantially identical to the third region of the third oligonucleotide; and
     (b) a second region that is suitable for use as a polymerase chain reaction (PCR) primer,
   wherein the third region of the third oligonucleotide and the first region of the fourth oligonucleotide have a melting temperature ($T_m$) that is at least about 5° C. higher than the $T_m$ of the second region of the fourth oligonucleotide,
   wherein the total length of the spacer of the third oligonucleotide and the first and second regions of the fourth oligonucleotide is at least about 45 nucleotides (nt) long, and wherein the first region of the first oligonucleotide is substantially different from the first region of the third oligonucleotide and the first region of the second oligonucleotide is substantially different from the first region of the fourth oligonucleotide.

8. The composition of claim 7, wherein the second region of the second oligonucleotide and the second region of the fourth oligonucleotide are suitable for amplifying a human genomic sequence.

9. An oligonucleotide comprising, in 5' to 3' order:
(a) a first region selected from the nucleic acid sequences of Table 1;
(b) a spacer that is between about 5 and about 15 nucleotides long; and
(c) a third region selected from the nucleic acid sequences of Table 2.

10. The oligonucleotide of claim 9, comprising a sequence of (SEQ ID NO: 9)
GTAAAACGACGGCCAGTATTTAGGTGACACTATAGACACTGACGACATGG

TTCTACA or (SEQ ID NO: 10)
AACAGCTATGACCATGCAGTCAAGTAACAACCGCGATACGGTAGCAGAGA

CTTGGTCT.

11. A method for amplifying a nucleotide sequence, comprising:
(i) incubating a target nucleotide template with a first and third oligonucleotides each comprising, in 5' to 3' order,
(a) a first region suitable for use as a Sanger sequencing primer;
(b) a spacer that is between about 5 and about 15 nucleotides long; and
(c) a third region suitable for use as a next generation sequencing (NGS) primer, and
a second and fourth oligonucleotides comprising, in 5' to 3' order,
(d) first regions that are substantially identical to the third region of the first or third oligonucleotide, respectively; and
(e) second regions which, in combination, suitable for amplifying the target nucleotide template as a pair of polymerase chain reaction (PCR) primers,
wherein the third regions of the first and third oligonucleotides and the first regions of the second and fourth oligonucleotides have a melting temperature ($T_m$) that is at least about 5° C. higher than the $T_m$ of the second regions of the second and fourth oligonucleotide, and wherein the total length of the spacer of the first oligonucleotide and the first and second regions of the second oligonucleotide is at least about 45 nucleotides (nt) long and the total length of the spacer of the third oligonucleotide and the first and second regions of the fourth oligonucleotide is at least about 45 nucleotides (nt) long, and wherein the first region of the first oligonucleotide is substantially different from the first region of the third oligonucleotide and the first region of the second oligonucleotide is substantially different from the first region of the fourth oligonucleotide;

(ii) performing a plurality of PCR cycles with a first annealing temperature ($T_a$) suitable for amplification using the second regions of the second and fourth oligonucleotides as primers; and (iii) performing a plurality of PCR cycles with a second annealing temperature ($T_a$) suitable for amplification using the third regions of the first and third oligonucleotides as primers.

12. The method of claim 11, wherein the first regions of the first and third oligonucleotides are selected from Table 1.

13. The method of claim 11, wherein the first regions of the third and fourth oligonucleotides are selected from Table 2.

14. The method of claim 11, wherein the first Ta is between about 53° C. and about 57° C.

15. The method of claim 11, wherein the second Ta is between about 59° C. and about 63° C.

16. The method of claim 11, wherein the ratios of concentrations of the first oligonucleotide to the second oligonucleotide and the third oligonucleotide to the fourth oligonucleotide are less than about 1:1.

17. A composition or kit, comprising a first and second oligonucleotides each comprising, in 5' to 3' order,
(a) a first region suitable for use as a Sanger sequencing primer;
(b) a spacer that is between about 5 and about 15 nucleotides long; and
(c) a third region suitable for use as a next generation sequencing (NGS) primer,
wherein the first regions of the first and second oligonucleotides are substantially different and the third regions of the first and second oligonucleotides are substantially different, and wherein the third regions of the first and second oligonucleotides are selected from Table 2.

18. The composition or kit of claim 17, wherein the first regions of the first and second oligonucleotides are selected from Table 1.

* * * * *